(12) United States Patent
Yang et al.

(10) Patent No.: US 7,655,779 B2
(45) Date of Patent: *Feb. 2, 2010

(54) COLLAPSIN RESPONSE MEDIATOR PROTEIN-1 (CRMP-1) TRANSCRIPTIONAL REGULATORY NUCLEIC ACID SEQUENCES

(75) Inventors: Pan-Chyr Yang, Taipei (TW); Tse-Ming Hong, Taipei (TW); Jeremy J. W. Chen, Fongyuan (TW); Cheng-Chung Wu, Sanchong (TW); Jin-Yuan Shin, Taipei (TW); Yi-Jen Lee, Hou-Bi Tainan (TW)

(73) Assignee: Advpharma Inc., Taipei Hsien (TW)

( * ) Notice: Subject to any disclaimer, the term of this patent is extended or adjusted under 35 U.S.C. 154(b) by 61 days.

This patent is subject to a terminal disclaimer.

(21) Appl. No.: 11/785,701

(22) Filed: Apr. 19, 2007

(65) Prior Publication Data

US 2007/0224681 A1 Sep. 27, 2007

Related U.S. Application Data

(62) Division of application No. 11/051,328, filed on Feb. 7, 2005, now Pat. No. 7,211,660.

(60) Provisional application No. 60/544,682, filed on Feb. 17, 2004.

(51) Int. Cl.
C07H 21/02 (2006.01)
(52) U.S. Cl. .................................. 536/23.1
(58) Field of Classification Search ............... 536/23.1
See application file for complete search history.

(56) References Cited

U.S. PATENT DOCUMENTS 6,812,339 B1 * 11/2004 Venter et al. ............. 536/24.31
7,211,660 B2 * 5/2007 Yang et al ................. 536/24.1

OTHER PUBLICATIONS

Li, Wei et al.; Analysis of the *Caenorhabditis elegans* Axonal Guidance and outgrowth Gene *unc-33*: Genetics Society of America; 1992, vol. 132, pp. 675-689.
Inagaki, Hiroshi et al.; Differential expression of dihydropyrimidinase-related protein genes in developing and adult enteric nervous system; Histochem Cell Biol, 2000, vol. 113, pp. 37-41.
Matsuo, Tatsuya et al.; Structure and promoter Analysis of the human *unc-33*-like Phosphoprotein Gene; The Journal of Biological Chemistry, 2000, vol. 275, No. 22, pp. 16560-16568.
Torres, Rosarelis et al.; Genomic Organization and Localization of the Human CRMP-1 Gene; DNA Research, 1998, vol. 5, pp. 393-395.
Quach, Tam et al.; Collapsin response mediator protein-3/unc-33-like rpotein-4 gene: organization, chromosomal mapping and expression in the developing mouse brain; GENE, 2000, vol. 242, pp. 175-182.
Byk, Tamara et al.; The Ullp family phosphoproteins Common and specific properties; Eur. J. Biochem., 1998, vol. 254, pp. 14-24.
Shih, Jin-Yuan et al.; Collapsin Response Mediator Protein-1 and the Invasion and Metastasis of Cancer Cells; Journal of the National Cancer Institute; 2001, vol. 93, No. 18, pp. 1392-1400.
Chu, Yi-Wen et al.; Selection of Invasive and Metastatic Subpopulations from a Human Lung Adenocarcinoma Cell Line; Am. J. Respir, Cell Mol. Biol., 1997, vol. 17. pp. 353-360.
Shih, Jin-Yuan et al.; Collapsin response mediator protein-1: A novel invasion-suppressor gene; Clinical & Experimental Metastasis, 2003, vol. 20, pp. 69-76.
Blanchette, Mathieu et al.; Discovery of Regulatory Elements by a Computational Method for Phylogenetic Footprinting; Genome Research, 2002, vol. 12, pp. 739-748.
Buratowshi, Stephen et al.; Mobility Shift DNA-Binding Assay Using Gel Electrophoresis; Current Protocols in Molecular Biology, 1996, unit 12.2, pp. 12.2.1-12.2.11.
Dignam, John David et al.; Accurate transcription initiation by RNA polymerase II in a soluble extract from isolated mammalian nuclei; Nucleic Acids Research; 1983, pp. 1475-1489.
Carthew, Richard W. et al.; An RNA Polymerase II Transcription Factor Binds to an Upstream Element in the Adenovirus Major Late Promoter; Cell, 1985, vol. 43, pp. 439-448.
Kristie, Thomas M. et al.; α4, the major regulatory protein of herpes simplex virus type 1, is stably and specifically associated with promoter-regulatory domains of α genes and of selected other viral genes; Proc. Nat. Acad. Sci. USA, 1986, vol. 83, pp. 3218-3222.

* cited by examiner

*Primary Examiner*—Sean E Aeder
(74) *Attorney, Agent, or Firm*—Hsiu-Ming Saunders; Intellectual Property Connections, Inc.

(57) ABSTRACT

This invention provides a transcription unit which is isolated from the upstream nucleic acid sequence of the collapsing response mediator protein-1 (CRMP-1) gene, an invasion-suppressor gene. The transcription unit contains a nucleic acid regulatory sequence which demonstrates promoter and/or regulatory activities (such as providing a transcription factor binding site) to enhance the expression of the CRMP-1 and/or a reporter protein. The invention also provides a DNA construct containing this transcription unit which can be transfected into a host cell. Additionally, the invention provides methods to enhance the expression of CRMP-1 and/or the reporter protein. The over-expression of CRMP-1 in a cancer cell can inhibit the metastasis of the cancer cell.

10 Claims, 7 Drawing Sheets

```
100  GGAAGCGCTTCCTGGTTCGAGCCGAGAGGGGCGAATCCGGCTTCGCTCCGCGCCGCCGGG
                  *                                *

-130 AGGAGCTGTCTGCAGCCCCCTCCTCCCGCCCTCGCCTCTCCCTCCTCCTTCTCCCGCCCT
       *  NF-E      Sp1       Sp1                              Sp1

-70  CCTCGCCGATCCGGGCGGTGCTGGCAGCCGGAGCGGCGGCGGGCGGGCCGAGCAGCCGGG
            Sp1              *    Sp1 Sp1    *

-10  GCAGCCGCGC GTGGGCATCCACGGGCGCCGAGCCTCCGTCCGTGTCTCTATCCCTCCCGG
       Sp1
```

RELATED APPLICATION

This application is a Divisional Application of U.S. patent application Ser. No. 11/051,328, filed on Feb. 7, 2005, now U.S. Pat. No. 7,211,660, which in turn claims the priority of U.S. Provisional Application Ser. No. 60/544,682, filed on Feb. 17, 2004, which are herein incorporated by reference.

FIELD OF THE INVENTION

The present invention relates to a transcription unit which is isolated from the upstream nucleic acid sequence of a collapsing response mediator protein-1 (CRMP-1) gene, preferably a human CRMP-1 gene or crmp-1. CRMP-1 gene is an invasion-suppressor gene, which prevent cancer metastasis. The transcription unit contains a nucleic acid regulatory sequence, which demonstrates promoter and/or regulatory activities (such as providing a transcription factor binding site) to enhance the expression of the CRMP-1 and/or an exogenous gene operatively linked to the transcription unit (such as a reporter protein). The invention also provides a DNA construct containing the transcription unit and a vector. The DNA construct can transfect a host cell. Additionally, the invention provides methods to enhance the expression of CRMP-1 and/or the reporter protein. The over-expression of CRMP-1 in a cancer cell can inhibit the metastasis of the cancer cell.

BACKGROUND OF THE INVENTION

Collapsin response mediator proteins (CRMPs) belong to a family of phosphoproteins, which mediate semaphorin/collapsin-induced growth cone collapse and are believed to be involved in both axonal guidance and neuronal differentiation. CRMPs are expressed mainly in the nervous system, especially during embryogenesis. Immunocytochemical studies have shown that CRMPs are distributed in the lamellipodia and filopodia of the growth cone, the shaft of axons, and the neuronal cell body. Their expression and phosphorylation are spatially and temporally regulated during development although their molecular mechanisms of action are yet to be clearly.

The members of CRMPs bear the sequence homology to UNC-33, a nematode protein, whose absence produces aberrant elongation of axons and uncoordinated movement in the worm *Caenorhabditis elegans*. (Li et al., *Genetics* (1992), 132(3): 675-689). CRMP family members have a 50%-70% amino acid sequence homology. Five members of the CRMP gene family (crmp-1, crmp-2, crmp-3, crmp-4, and crmp-5), encoding closely related 60-66 kDa proteins, have been independently cloned by various laboratories. Each CRMP is believed to have a unique function. The members of the CRMP family have been referred to as CRMP (collapsin response mediator protein), TOAD-64 (turned on after division of a 64 kD protein), Ulip (UNC-33 like phosphoprotein), DRP (dihydropyrimidinase related protein) and TUC (TOAD/Ulip/CRMP). Nonetheless, the most frequently used name in medical literature is CRMP.

Transcription of the CRMP gene is differentially regulated. (Kato et al., *Histochem. Cell Biol*. (2000), 97(11):6212-6217; Matsuo et al., *J. Biol. Chem*. (2000), 275(22):16560-16568; Quach et al., *Gene* (2000), 242(1-2): 175-182). Mouse CRMP-1, CRMP-4 and CRMP-5 are mainly expressed in the fetal brain and not in the brain of the adult mice. On the other hand, CRMP-2 and CRMP-3 are expressed in the brain of both the fetal and the adult mice. However, in the adult mice, CRMP-3 is localized in the cerebellum. In PC-12 cells, after induction of neuronal differentiation by nerve growth factor (NGF), CRMP-4 was strongly up-regulated, whereas CRMP-1 and CRMP-2 only increased slightly and CRMP-3 was down-regulated. (Byk et al., *Eur. J. Biochem*. (1998), 254(1): 14-24). At this time, only the promoter of human CRMP-4 has been isolated and analyzed. (Matsuo et al., *J. Biol. Chem*. (2000), 275(22): 16560-16568). No studies of the regulatory elements of other members of the CRMP family have been conducted.

Collapsin response mediator protein-1 (CRMP-1), also named as dihydropyrimidinase related protein-1 (DRP-1), is a 62 kDa phosphoprotein. CRMP-1 was originally discovered in the brain tissue and thought to be a brain specific protein involved in the collapsin-induced growth cone collapse during neural development. (Torres et al., *DNA Res*. (1998), 5(6): 393-395).

Recently, the inventors of the present invention discovered that the level of expression of the gene encoding CRMP-1 (hereinafter "CRMP-1 gene") inversely affects cancer invasion and metastasis, (i.e., the higher the level of expression, the lower the incidence of cancer invasion and metastasis) and thus characterized the CRMP-1 gene as an invasion-suppression gene. (Shih et al., *J. Natl. Cancer Inst*. (2001), 93(18): 1392-1400; Chu et al., *Am. J. Respir. Cell Mol. Biol*. (1997), 17: 353-360; and Shih et al., *Clinical & Exper. Metastasis* (2003) 20: 69-76). The contents of these articles are herein incorporated by reference. The inventors of the present invention found that low-expression patients of CRMP-1 had more advanced diseases and lymph node metastases, while high-expression patients of CRMP-1 had a significantly longer disease-free and overall survival period.

In the invention to be presented in the following sections, the findings of the nucleic acid regulatory elements/sequences associated with the CRMP-1 gene are disclosed. These nucleic acid regulatory elements/sequences include, but are not limited to, the promoter, the basal transcription regulatory region, and the transcription factor binding sites which are located upstream of, and are operatively linked to, the CRMP-1 gene. Understanding the regulation of the expression of the CRMP-1 gene will lead to new strategies for treatment of cancer patients so as to halt cancer metastasis.

SUMMARY OF THE INVENTION

The present invention provides a transcription unit, which comprises a nucleic acid regulatory sequence that is isolated from upstream (i.e., at the 5'-flanking region of the gene) of the gene encoding a collapsin response mediator protein-1 ("CRMP-1 gene"). The nucleic acid regulatory sequence is characterized by its ability to regulate expression of the CRMP-1 gene and/or an exogenous gene that is/are operatively linked to the nucleic acid regulatory sequence. The CRMP-1 gene is preferably a human CRMP-1 gene. The nucleic acid sequence encoding CRMP-1 protein can be found in SWISS-PROT entry Q14194, GenBank locus D78012, and GenBank locus BAA11190, and is disclosed as SEQ ID NO: 24.

In one embodiment, the nucleic acid regulatory sequence comprises the nucleic acid sequence of SEQ ID NO:2, which includes the nucleotides at positions −1920 to +50 upstream from the CRMP-1 gene. This nucleic acid sequence represents the entire promoter region. The transcription start nucleotide of the CRMP-1 gene is designated as +1, with the ATG start codon at positions +151 to +153.

In yet another embodiment, the nucleic acid regulatory sequence comprises the nucleic acid sequence of SEQ ID NO:3, which includes the nucleotides at positions −180 to +50 upstream from the CRMP-1 gene. This nucleic acid sequence represents the minimal promoter sequence.

In yet another embodiment, the nucleic acid regulatory sequence comprises the nucleic acid sequence of SEQ ID NO:5, which includes the nucleotides at positions −133 to −122 upstream from the CRMP-1 gene. This nucleic acid sequence contains a first regulatory factor binding site having the nucleic acid sequence of GGGAGGAG. A loss of or a mutation in this nucleic acid sequence results in drastic reduction in expression of the CRMP-1 gene and/or the exogenous gene.

In yet another embodiment, the nucleic acid regulatory sequence comprises the nucleic acid sequence of SEQ ID NO:6, which includes the nucleotides at positions −115 to −100 upstream from the CRMP-1 gene. This nucleic acid sequence contains a second regulatory factor binding site having the nucleic acid sequence of CTCCTCCC, which is the inverted sequence of GGGAGGAG that found in the first regulatory factor binding site. A loss of the second transcription factor binding site (SEQ ID NO:6) in addition to the first transcription factor binding site (SEQ ID NO:5) results in further reduction of CRMP-1 gene and/or the exogenous gene expression. However, a mutation in the second transcription factor binding site does not appear to affect the transcriptional activities of the CRMP-1 gene and/or the exogenous gene.

The exogenous gene that can be operatively linked to the nucleic acid regulatory sequence can be a reporter gene, such as the firefly luciferase gene or the green fluorescent protein gene.

The present invention also provides a DNA construct which comprises the nucleic acid regulatory sequence, such as SEQ ID NO:2, SEQ ID NO:3, SEQ ID NO:4 or SEQ ID NO:5, and a vector. An example of the vector for preparing the DNA construct is a pGL3-basic vector, which contains the firefly luciferase gene.

The present invention further provides a transfected cell, which comprises the DNA construct that contains the nucleic acid regulatory sequence in a host cell, such as a human cell, and preferably a human cancer cell, such as a human lung adenocarcinoma cell or a human colon cancer cell.

Additionally, the present invention provides a method for enhancing the expression of the CRMP-1 gene and/or the exogenous gene (such as the firefly luciferase gene) in a host cell. The method comprises transfecting the host cell with the DNA construct that contains the transcription unit. The host cell is preferably a human cell.

Finally, the present invention provides a method for inhibiting metastasis of a human cancer cell. The method comprises transfecting the human cancer cell with the DNA construct that contains the transcription unit.

BRIEF DESCRIPTION OF THE DRAWINGS

FIG. 2 shows a partial nucleic acid sequence (SEQ ID NO:22) representing the 5' flanking region of human CRMP-1 gene. A partial exon 1 of the human CRMP-1 gene is shown in the box. Potential transcription factors (NF-E and Sp1) binding sites are indicated as underlined sequences. The * represents the four nucleotides-GAGC.

FIG. 3 identifies the specific DNA-protein complexes binding in the CRMP-1 promoter region. These studies were conducted using electrophoretic mobility shift assay (EMSA), competition mobility shift assay, and antibody supershift assay, as described in Example 6, infra. Three double-stranded DNA probes were designed for the motility shift assay. DNA probe A contained tandem repeat of the first putative binding site sequence containing (5'-GGGAGGAGCTGTGGGAGGAGCTGT-3', SEQ ID NO:12). The underlined sequence denotes the first putative binding site sequence. DNA probe B contained the fragment from positions −117 to −100 (5'-AGCCCC CTCCTCCCGCCC-3', SEQ ID NO:13), containing a GGGAGGAG-inverted sequence. DNA probe C contained the fragment from positions −137 to −100(5'-CGCC GGGAGGAGCTGTCTGCAGCCCC CTCCTCCCGCCC-3', SEQ ID NO:14). All of the DNA probes were labeled with $^{32}P$ for standard binding reaction.

DETAILED DESCRIPTION OF THE INVENTION

Figure 1:
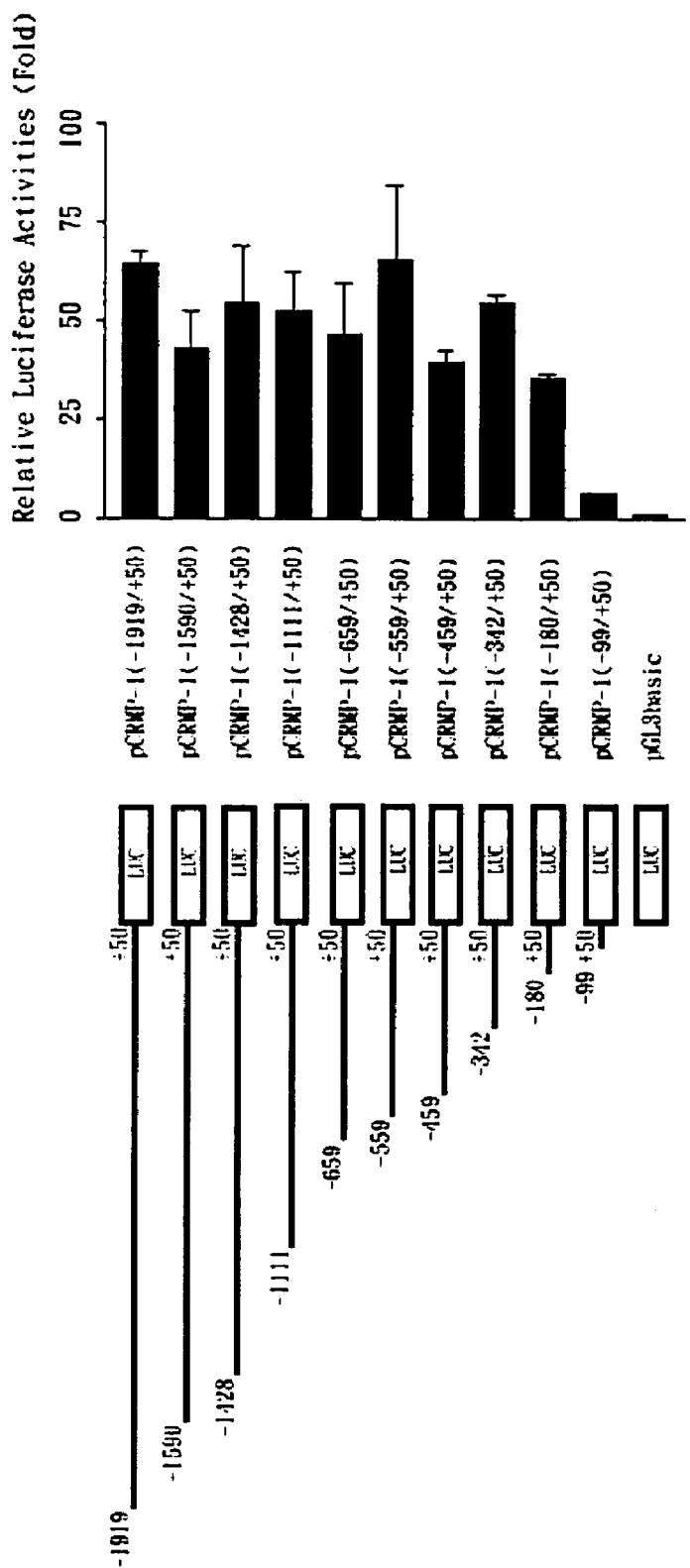
FIG. 1 shows the relative luciferase activities as a result of a series nucleotides deletions of the 5' flanking region of the human CRMP-1 gene after the DNA construct containing the designated nucleic acid regulatory sequence upstream from the CRMP-1 gene was transfected into a $CL_{1-0}$ cell line, which is a subline of a lung adenocarcinoma cell line. The relative luciferase activities were normalized by the β-galactosidase activities, and the values were subsequently compared with the mean values of the control plasmid (i,e., with pGL3basic only and without the nucleic acid regulatory sequence upstream from the CRMP-1 gene) to determine the % of expression vs. the control.

In describing the invention, the following specific terminology is employed for the sake of clarity. However, the invention is not intended to be limited to the specific terminology so selected. It is to be understood that each specific element includes all technical equivalents, which operate in a similar manner to accomplish a similar purpose.

The term "nucleic acid sequence", as used herein, refers to a DNA, cDNA or RNA molecule, either as a separate fragment or as part of a larger polynucleotide construct.

The term "gene" as used herein, refers to a polymer in which nucleotides encoding the amino acids constituting a polypeptide (e.g., enzyme) are joined into a linear structure with directionality. The "gene" may be single-stranded (e.g., RNA) or double-stranded (e.g., DNA). DNA may be, for example, cDNA which is enzymatically prepared from a transcribed RNA (mRNA), genomic DNA from chromosomes, or chemically synthesized DNA.

The term "nucleic acid regulatory sequence", as used herein, refers to the 5'-flanking region DNA, cDNA or RNA fragment(s) upstream from the gene which affect(s) the transcription and expression of the gene. Such nucleic acid regulatory sequence may include a promoter region for regulating the transcription of a coding region, an enhancer region affecting the promoter region, and other regulatory factor binding sites (e.g., transcription factor binding sites, such as a TATA Box, CCAAT Box, AP1, Sp1, or NF-κB binding sites) as well as intron or the like. The nucleic acid regulatory sequence may or may not be directly linked to the gene.

The term "promoter", as used herein, refers to a DNA sequence to which RNA polymerase is capable of binding to initiate transcription of the gene. A promoter may be linked to the gene with which it is naturally associated, or may be functionally linked to an exogenous gene. In this context, the term "exogenous gene" is intended to mean a nucleic acid sequence that encodes a product but does not naturally occur with the promoter sequence.

The term "operatively linked", as used herein, means that the nucleic acid regulatory sequence and the gene are functionally linked such that the nucleic acid regulatory sequence controls the expression of the gene.

The term "reporter gene" is used in molecular biology as indicators of gene activity. A reporter gene will typically encode an enzyme activity that is lacking in the host cell or organism, which is to be transformed. This allows the measurement or detection of the enzyme activity, which may be used as an indicator or "reporter" of the presence of expression of the newly introduced gene. A reporter gene may be put under the influence of a "controller" sequence, such as a promoter element. Successful expression of the reporter gene product serves as an indicator of controller element activity.

The present invention described a novel nucleic acid regulatory sequence which affects the expression of the gene encoding the collapsin response mediator protein-1 gene ("CRMP-1 gene"). A partial genomic sequence of the CRMP-1 gene which includes the 5'-flanking region of the genomic sequence of the CRMP-1 gene is designated as SEQ ID NO:1. SEQ ID NO:1 contains the nucleic acid sequence from positions −1920 to +189 of the CRMP-1 gene. This nucleic acid sequence possesses the entire promoter region, several regulatory factor binding sites, and exon-1 of the CRMP-1 gene (at positions +1 to +189 of the CRMP-1 gene) which contains the starting codon ATG (at positions +151-153 as shown in SEQ ID NO:1) encoding methionine.

The nucleic acid sequence at positions −1920 to +50 upstream of the CRMP-1 gene is designated SEQ ID NO:2. This nucleic acid sequence contains the entire promoter region, several transcription factor binding sites, and a partial sequence of the exon-1 of the CRMP-1 gene. However, it does not contain the starting codon ATG of the CRMP-1 gene.

The nucleic acid sequence at positions −180 to +50 upstream from the CRMP-1 gene is designated SEQ ID NO:3. This nucleic acid sequence contains the core promoter region and the transcription factor binding sites.

The nucleic acid sequence at positions −180 to −100 upstream from the CRMP-1 gene is designated SEQ ID NO:4. This nucleic acid sequence contains the minimal promoter region and the transcription factor binding sites.

The nucleic acid sequence at positions −133 to −122 upstream of the CRMP-1 gene is designated SEQ ID NO:5. This nucleic acid sequence comprises a first transcription factor binding site having the nucleic acid sequence of GGGAGGAG The nucleic acid sequence at positions −115 to −100 upstream from the CRMP-1 gene is designated SEQ ID NO:6. This nucleic acid sequence comprises a second transcription factor binding site having the nucleic acid sequence of CTCCTCCC, which is an inverted sequence of the first transcription factor binding site containing the nucleic acid sequence of GGGAGGAG The nucleic acid regulatory sequence that contains SEQ ID NO:1-6 regulates not only the expression of the CRMP-1 gene, but also the expression of an exogenous gene that is operatively linked to the nucleic acid regulatory sequence. The exogenous gene can be a reporter gene. Examples of the reporter gene includes a firefly luciferase gene, and green fluorescent protein (GFP) gene.

The firefly luciferase gene is a well-known reporter gene. The coding sequence of the firefly (*photinus pyralis*) luciferase has been cloned in the pGL3 Luciferase Reporter Vector and currently sold by Promega. This reporter gene provides a basis for the quantitative analysis of factors that potentially regulate mammalian gene expression. In the pGL3 Luciferase Reporter Vector (also known as pGL3 basic vector), the firefly luciferase gene coding region has been optimized for monitoring transcriptional activity in transfected eukaryotic cells. The assay of this genetic reporter is rapid, sensitive and quantitative.

Green Fluorescent Protein (GFP) gene is another well-known reporter gene. GFP is a protein produced by a jellyfish *Aequorea*, which fluoresces in the lower green portion of the visible spectrum. The gene for GFP has been isolated and has become a useful tool for making expressed proteins fluorescent by creating chimeric genes composed of those of GFP and its different color variants linked to genes of proteins of interest. One may thus have an in vivo fluorescent protein, which may be followed in a living system. GFP has several different color variants. The GFP and GFP color variant vectors for gene cloning and construction are available from Clontech.

The reporter gene can be operatively linked to the nucleic acid regulatory sequence of the present invention via vectors to form a DNA or expression construct, which can then be transfected into a host cell. Specific vectors, which can be used to form the DNA construct are known in the art and include either a plasmid or a virus carrier. When the firefly luciferase gene is used as the reporter gene, the use of the pGL3 Luciferase Reporter Vector currently sold by Promega is preferred. When the green fluorescent protein gene is used as the reporter gene, the use of pGFP Vector currently sold by Clontech is preferred.

In designing the DNA constructs, it is not necessary to include the entire nucleic acid regulatory sequence (at positions −1920 to +50, SEQ ID NO:2), which covers the entire promoter and other regulatory regions of the CRMP-1 gene. A core promoter region (at positions −180 to +50, SEQ ID NO:3) or a minimum promoter region (at positions −180 to −100, SEQ ID NO:4) have shown to provide significant regulatory effects on CRMP-1 or reporter protein production. In addition, the nucleic acid sequence of SEQ ID NO:5 (at positions −133 to −122) contains a regulatory factor binding site having the nucleic acid sequence of 5'-GGGAGGAG-3', which is preferred to be included in the DNA constructs.

The regulatory factor binding site could be a transcription factor binding site, such as the binding site for transcription factor Sp1. The SP1 transcriptional control sequence is found in a large number of viral and cellular promoters, including the HIV long terminal repeat. The SP1 transcription factor contains contiguous zinc finger motifs that provide specific DNA binding activity. Transcription factor Sp1 stimulates the basal activity of the minimal promoter through mechanisms that maintain the differential activity.

As shown by the electrophoretic mobility shift assay (EMSA), the competition mobility shift assay, the antibody supershift assay, and the reverse transcription-polymerase chain reaction (RC-PCR), as shown in Examples 6 and 7, infra, the nucleic acid regulatory sequence of the present invention has the ability to bind to various proteins. The binding of the various proteins affects the regulatory capacity of the nucleic acid regulatory sequence, which in turn may affect the expression of the CRMP-1 gene.

The following experimental designs are illustrative, but not limiting the scope of the present invention. Reasonable variations, such as those occur to reasonable artisan, can be made herein without departing from the scope of the present invention.

EXAMPLES

Example 1

Clonin of 5'-Flanking Region of CRMP-1 Gene and Construction of Recombinant Plasmids Construction of PCRMP-1 (−1920/+189).

A 2.1-kb DNA fragment containing the 5'-flanking region of hCRMP-1 gene (positions −1920 to +189 of human CRMP-1 gene (HCRMP-1), [SEQ ID NO:1]) was obtained by PCR amplification (Roche GC-rich PCR system) using two primers:

(1) 5'-CCGCTCGAGGCTTTGTACCGGCGAAATCT-3' (sequence complementary to position −1920 to −1901, with an artificial XhoI site at the 5'-end, [SEQ ID NO:7]); and (2) 5'-CCCAAGCTTCGTGATTGTGCGGGATGCTCT-3' (positions +170 to +189, with an artificial Hind III site at the 5'-end [SEQ ID NO:8]).

The human BAC clone RP 11-69D13 (Invitrogen) was used as DNA template. This amplified fragment was cleaved with XhoI and HindIII and inserted into the XhoI/HindIII site at the upstream of luciferase gene of the pGL3-basic vector (Promega). The construct was designated as pCRMP-1 (−1920/+189) and the sequence of the amplified fragment was confirmed by sequence analysis.

Construction of PCRMP-1 (−1920/+50).

The 5'-flanking region of hCRMP-1 gene (positions −1920 to +50 of hCRMP-1, [SEQ ID NO:2]) was amplified by using two PCR primers:

(1) 5'-CGCTAATTACGCCAGCCCAAG-3' (positions 5023 to 5042 of pGL3-basic vector, [SEQ ID NO:9]) and (2) 5'-CCCAAGCTTCCGGGAGGGATAGAGACAC-3' (positions +32 to +50, with an artificial XhoI site at the 5'-end, [SEQ ID NO:10]). The plasmid pCRMP-1(−1920/+189) was used as template DNA. This amplified DNA fragment was first digested with NotI and HindIII restriction endonucleases and inserted into the NotI/HindIII site of the pGL3-basic vector (Promega). The construct was designated as pCRMP-1(−1920/+50) and the sequence of the amplified fragment was confirmed by sequence analysis.

Example 2

Transient Transfection and Luciferase Reporter Assay

Human lung adenocarcinoma cells ($CL_{1-0}$) were plated out at a cell density of $1\times10^5$ cells/well of a 6-well culture plate and maintained in RPMI 1640 medium (RPMI) supplemented with 10% fetal bovine serum (FBS; Invitrogen) for 24 hours prior to transfection. One microgram of pCRMP-1(–1920/+50) DNA and 1 µg of internal control plasmid DNA (pSV-β-galactosidase) were dissolved in serum free RPMI and complexed with 10 µl Lipofectamine (Invitrogen). The DNA/lipid complexes were allowed to anneal at room temperature for 45 minutes prior to their addition to $CL_{1-0}$ cells. Cells were co-transfected by incubation with complexes for 6 hours at 37° C., 5% $CO_2$. Medium was removed and cells which were washed twice with 1×PBS. 2 ml of RPMI supplemented with 10% fetal bovine serum were added to the cells to be incubated at 37° C., with 5% $CO_2$. Cells were harvested after 36 hours of incubation and cellular extracts were obtained by using 250 µl of lysis buffer (Tropix, Inc.) per well.

Human colon cancer cell lines CCM1, CCM2, and CCM3 were provided by the Food Industry Research and Development Institute (FIRDI) in Taiwan. These cell lines were deposited at the FIRDI in Taiwan and registered with the numbers BCRC 60448, BCRC60449, and BCRC60450. Human colon cancer cells were plated according to the procedures well known to the artisans in the field. The cells were transfected with pCRMP-1 containing the full length CRMP-1 promoter (–1920/+50) and harvested according to the procedures described above.

For determination of luciferase and β-galactosidase activities, 20 µl of cell extract were separately used. The assays were carried out by Luciferase assay kit and Galacto-Light Plus™ system (Tropix, Inc.) on the luminometer (BERTHOLD Detection Systems Type Sirius 2C, Pforzheim, Germany).

Luciferase activity mentioned in the following texts represents data that has been normalized with β-galactosidase activity. The luciferase activity was used as an indication of gene expression in cells containing the indicated reporter DNA construct.

Example 3

Analysis of The Nucleic Acid Regulatory Sequence of CRMP-1 Gene

Sequential Truncation of 5'-flanking region upstream of the CRMP-1 gene

Sequential deleted 5' regulatory sequence mutants of CRMP-1 gene were constructed using the following method, to determine the function of the hCRMP-1 regulatory elements. All of the procedures shown below were according to the instructions in the Exo Mung Bean Deletion Kit (Stratagene) with some modifications. Briefly, the pCRMP-1(–1920/+50) was first digested with restriction endonucleases XhoI. The linealized plasmids were further treated with exonuclease III at 37° C. for different time intervals. Nine different sizes of plasmid fragments starting from position –1920 were obtained after phenol-chloroform extraction. The truncated plasmid fragments were then incubated with mung bean nuclease for 30 minutes at 37° C. after inactivation of the exonuclease III at 68° C. for 15 minutes. The resulting plasmid fragments were precipitated and ligated by T4 DNA ligase. Each truncated construct was transiently transfected into $CL_{1-0}$ cells and its relevant luciferase activity was determined as described in Example 2.

Results:

The Transcriptional Activities of Various Truncated Regulator Y Sequences.

The various constructs and their relevant luciferase activities in transfected human lung adenocarcinoma cells ($CL_{1-0}$) were depicted schematically as shown in FIG. 1. The luciferase activities in various human colon cancer cells transfected with pCRMP-1 containing the full length CRMP-1 promoter (–1920/+50) were also detected (data not shown). Luciferase activity was firstly normalized to β-galactosidase activity. The luciferase activity of cells transfected with control plasmid pGL3basic was set as baseline.

Deletion of nucleotides –1920 to –180 did not significantly change the transcriptional activity, as compared to that of the pCRMP-1(–1920/+50) in $CL_{1-0}$. The fragment from –180 to +50 exhibited promoter activity. Cells transfected with DNA constructs containing the reporter gene and the regulatory region from positions –99 to –180 were shown to enhance the transcriptional activities to 30~60 fold, in comparison to those in cells containing the control plasmid pGL3basic. Specifically, the transcriptional activities of the DNA construct pCRMP-1 (–180/+50) containing the nucleotides at positions –99 to –180 was increased up to 5-fold more than the activity of the pCRMP-1(–99/+50).

Example 4

Identification of Regulatory Factor Binding Sites

The primary sequence analysis of the 5'-flanking region of the CRMP-1 gene revealed that it was a TATA-less promoter. Several regulatory factor binding sites, such as Sp1 binding site, were predicted to be in the region between positions –188 and –99 with the help of a web tool Transcription Element Search System (TESS; provided by the Computational Biology and Informatics Laboratory at the University of Pennsylvania). Two regulatory factor binding sites containing GGGAGGAG-element were identified. This element has been listed as putative regulatory elements by a computational method for phylogenetic footprinting (Blanchette, M. and Tompa, M.: Discovery of regulatory elements by a computational method for phylogenetic footprinting. *Genome Research*, 12 (5): 739-748 (2002). The first regulatory factor binding site was located in the regions between positions –133 to –122 (5'-<u>GGGAGGAG</u>CTGT-3', SEQ ID NO:5). The second one is in the region from positions –115 to –100 (5'-CCCC<u>CTCCTCCC</u>GCC-3', SEQ ID NO:6) containing a <u>GGGAGGAG</u>-inverted sequence overlapped with other putative Sp1 binding site.

Results:

Deletion study of the regulatory factor binding sites. Two deletion DNA constructs, pCRMP-1(–116/+50) and pCRMP-1(–99/+50), were designed by removal of the first regulatory factor binding site and both sites, respectively. As shown in Table 1, the loss of the fragment between –180 to –117, which contains the first regulatory factor binding site, resulted in the reduction of almost 60% of the relative luciferase activity (pCRMP-1(–116/+50). The further 10 reduction up to 75% was observed after removal of both regulatory factor binding sites in pCRMP-1(–99/+50), as shown also in Table 1. These results indicated that both of the regulatory factor binding sites were essential for the basal transcriptional activity of the CRMP-1 gene promoter.

TABLE 1

Deletion and Modified DNA Constructs Containing a Reporter Gene Encoding Luciferase and Their Relevant Luciferase Activity

| Reporter Construct | Description | Rel. A(luc), % |
|---|---|---|
| pCRMP-1(−180/+50) | Containing the core promoter sequence described as the wild type DNA construct in the mutation studies | 100 |
| pCRMP-1(−99/+50) | Loss of crucial part of sequence | 24 ± 10 |
| pCRMP-1(−116/+50) | Deletion of the fragment between −180 to −117 (containing the first regulatory factor binding site) | 42 ± 3 |
| pCRMP-1-M12 | Addition of tandem repeat of the first regulatory factor binding site to 5' end of the DNA construct pCRMP-1(−99/+50) | 114 ± 4 |

Note:
Rel. A(luc) = Relative Luciferase Activity

Recovery of the Transcriptional Activity by Adding an Artificial Tandem Repeat Containing the First Regulatory Factor Binding Site to the DNA Construct The DNA construct pCRMP-1-M12 contained the original nucleic acid regulatory sequence at positions −99 to +50 and two additional artificial tandem repeat of the first regulatory factor binding site, which was at positions −133 to −122 upstream of the CRMP-1 gene.

A short oligonucleotide flanking with XhoI restriction sequence (5'-CCGCTCGA GGGGAGGAGCTGT GGGAGGAGCTGT CTCGAGCGG-3', SEQ ID NO:11)

and its reverse sequence were chemically synthesized to form a short DNA double strand. The modified DNA construct (i.e., pCRMP-1-M12) was obtained by digestion of the double stranded oligonculeotide with endonuclease XhoI followed by ligation to the linearized (also with XhoI digested) DNA construct pCRMP-1(−99/+50). The relative luciferase activity of this mutant construct was 114% as compared to the wild-type DNA construct (See Table 1). This result clearly demonstrated that the addition of the 2 first regulatory factor binding sites not only restored but also in fact enhanced the expression capability of pCRMP-1(−99/+50) to the level of the wild type DNA construct pCRMP-1(−180/+50). (See Table 1).

Without the addition of the first regulatory factor binding site, the DNA construct pCRMP-1(−99/+50) showed about 24% relative luciferase activity and was used as a negative control, as opposite to the wild type pCRMP-1 (−180/+50) used as positive control (i.e., the luciferase activity of pCRMP-1(−180/+50) was used as 100%). (See Table 1). This result further suggests that the first regulatory factor binding site was crucial to the transcription and expression of the human CRMP-1 gene. Specifically, these two artificial tandem repeats of the first regulatory factor binding site could substitute the region for original sequence without any effect on relevant luciferase activity. Furthermore, the transcription and expression activity of this first regulatory factor binding site did not appear to be dependent on the exact position from the transcription start site of the CRMP-1 gene (i.e., the ATG start codon of exon-1 of the CRMP-1 gene).

Example 5

Functional Analysis of Human CRMP-1 Basal Promoter Using Site-Directed Mutagenesis Site-directed mutagenesis method was applied for further sequence structure studies of possible binding sites in the nucleic acid regulatory sequence at positions −180 to −100 upstream from the CRMP-1 gene.

Methods and Results:

The methods of making the mutant DNA constructs were shown below and the results of the mutant DNA constructs and their relevant luciferase activities are depicted in Table 2.

Mutations in the first regulatory factor binding site (Positions −133 to −122)

Five mutant DNA constructs containing the reporter gene luciferase were designed on the base of the wild type DNA construct pCRMP-1(−180/+50). They were designated as pCRMP-1 M3, m3-2, m3-3, m3-4, and m3-5. All of them had the same length of 5' end CRMP-1 promoter as the DNA construct pCRMP-1(−180/+50) except that each mutant represented a point mutation or a nucleic acid conversion which occurred at positions −133 to −122, as indicated in Table 2. As shown in Table 2, the relative luciferase activities of mutants M3 and m3-4 were drastically reduced to almost half of that of the wild type (WT) DNA construct pCRMP-1(−180/+50). In addition, the mutations in mutants m3-2 and m3-3 demonstrated a reduction in transcription and expression activity of about 70% to 60%, respectively. (See Table 2). Moreover, the mutant construct M11, although having the same mutations as that of the pCRMP-1 M3, demonstrated an obvious loss (50%) of the relative luciferase activity, even though the 1.9 kb upstream regulatory sequence was intact in the DNA construct.

Mutations in the Second Regulatory Factor Binding Site (Positions −115 to −100)

The second regulatory binding site contains a GGGAG-GAG-inverted sequence. No any obvious effects on the transcriptional activities were observed when the sequence structure at the region from position −115 to −100 (i.e., DNA constructs pCRMP1 M4 and M5) were disrupted. (See Table 2).

Mutations in Regions Other Than the Two Regulatory Factor Binding Sites

The mutant construct pCRMP-1 M1 with the mutations at the positions −171 and −170 (conversion of AG to GA) showed a reduction of transcription activity to 60%, as compared to that of the wild type DNA construct pCRMP-1(−180/+50). (See Table 2). A slight (i.e., about 20% reduction) loss of the transcription activity was observed, as the conversion of GC to AT at the positions −119 and −118 was conducted. (See Table 2). In addition, the transcription activity of the CRMP-1 gene was not effected when mutations were at positions −146 and −145 (i.e., with conversion of CT to TC) (Table 2, M2), at positions −135 and −134 (i.e., with conversion of CC to TT) (Table 2, m3-6), and at positions −121 and −120 (i.e., with conversion of CT to TC) (Table 2, m3-5).

TABLE 2

Functional Analysis of Human CRMP-1 Basal
Promoter Using Site-Directed Mutagenesis

| DNA Constructs*[1] | Rel. A(luc)*[2] | Mutation sites | Substitutions |
|---|---|---|---|
| Wt | 100 | *** | *** |
| M1 | 65 ± 6 | −171, −170 | ag => ga |
| M2 | 115 ± 7 | −146, −145 | ct => tc |
| M3 | 43 ± 2 | −127, −126 | ag => ga |
| m3-2 | 73 ± 10 | −131, −130 | ga => ag |
| m3-3 | 63 ± 4 | −123, −122 | gt => ac |
| m3-4 | 49 ± 7 | −133, −132 | gg => aa |
| m3-5 | 103 ± 38 | −121, −120 | ct => tc |
| m3-6 | 108 ± 23 | −135, −134 | cc => tt |
| m3-7 | 80 ± 10 | −119, −118 | gc => at |
| M4 | 85 ± 22 | −113, −111, −109 | c => t, c => t, c => t |
| M5 | 107 ± 19 | −105, −103, −101 | c => t, g => t, c => t |
| M11 | 51 ± 7 | −127, −126 | ag => ga |

*[1]Abbreviation for mutant reporter DNA constructs. They were based on the wild type construct pCRMP-1(−180/+50), except M11, which was based on pCRMP-1(−1920/+50).
*[2]Rel. A(luc) for relative luciferase activity in percentage. The relative activity of all reporter DNA constructs, with the exception of M11, were based on the activity of wild type DNA construct pCRMP-1(−180/+50) (as 100%). The reference for the relative activity of reporter DNA construct M11 was the wild type pCRMP-1(−1920/+50).
*** means no mutation and no substitution In sum, the results of the site-directed mutagenesis confirmed that the first regulatory factor binding site at positions −133 to −122 (5'-GGGAGGAGCTGT-3', SEQ ID NO:5) was essential for the regulation of the transcription and/or expression activity of the CRMP-1 gene.

Example 6

Analysis of DNA-binding Proteins of the CRMP-1 Gene Nucleic Acid Regulatory Fragments Material and Methods The major technique for identifying specific binding protein complexes in the nuclear extracts of the crmp-1 regulatory fragments was electrophoretic mobility shift assay (EMSA). Its related method, antibody super-shift assay, further confirmed the involvement of the binding proteins (i.e., in the formation of DNA-protein complexes) in the CRMP-1 gene nucleic acid regulatory sequence.

Electrophoretic mobility shift assay (EMSA), or gel shift assay, provides a simple method for detecting DNA-binding proteins such as transcription factors (Buratowski et al., *Current Protocols in Molecular Biology*, (1996): 12.2.1-12.2.11). This assay is based on the observation that DNA-protein complexes migrate through a non-denaturing polyacrylamide gel more slowly than free DNA fragments or double-stranded oligonucleotides. The gel shift assay was performed by incubating a purified protein, or a complex mixture of proteins (such as from cell nuclear extracts), with a $^{32}$P end-labeled DNA fragment containing the regulatory factor binding site. The specificity of the DNA-binding protein for the regulatory factor binding site was confirmed by competition experiments using unlabeled DNA fragments or oligonucleotides containing the regulatory factor binding sites of the CRMP-1 gene or other unrelated DNA sequence.

Preparation of Nuclear Extracts.

Two different nuclear extracts were applied for the assays, which were HeLa nuclear extracts (Promega, USA) and $CL_{1-0}$ nuclear extracts. They were prepared according to the method described by Dignam et al. (1983) (Dignam et al., *Nucleic Acids Res.*, (1983), 11, 1475-1489).

DNA Probes and Radioactive Labeling.

Three double-stranded DNA probes were designed specifically for the motility shift assay. They were generated by chemical synthesis and annealing of the complementary oligonucleotides.

DNA probe A contained tandem repeat of the first regulatory factor binding site sequence (5'-GGGAGGAGCTGT GGGAGGAGCTGT -3', SEQ ID NO:12).

DNA probe B was the fragment from positions −117 to −100 (5'-AGCCCCCTCCTCCCGCCC-3', SEQ ID NO:13), containing a GGGAGGAG-inverted sequence.

DNA probe C was the fragment from positions −137 to −100 (5'-CGCCGGGAGGAGCTGTCTGCAGCCCC CTCCTCCCGCCC-3', SEQ ID NO:14).

Radioactive labeling of DNA probes was performed according to the instructions of Gel Shift Assay Systems (Technical Bulletin No. 110) provided by Promega (USA).

Procedures for DNA-Protein binding reactions and electrophoresis were according to the instructions of Gel Shift Assay Systems (Technical Bulletin No. 110; Promega) with a few modifications. Standard DNA-Protein binding reaction was started with the incubation of 1-20 µg of HeLa nuclear extract or $CL_{1-0}$ nuclear extract at room temperature for 10 minutes in a binding buffer (4% glycerol, 1 mM MgCl2, 0.5 mM EDTA, 0.5 mM DTT, 50 mM NaCl, 10 mM Tris-HCl (pH 7.5), 0.05 mg/ml poly(dI-dC)·poly(dI-dC)). Each reaction mixture was then mixed with a $^{32}$P-labeled probe and then incubated at room temperature for another 20 minutes. A tenth volume of a gel loading buffer, containing 250 mM Tris-HCl, (pH 7.5), 0.2% bromophenol blue, and 40% glycerol, was added to each reaction mixture. Samples were electrophoresed for 100V at 4° C. after pre-running on the 4% PAGE gel in 1XTBE buffer.

Competition Mobility Shift Assay.

The assessment of the nucleic acid sequence specificity of protein-DNA interactions were achieved by applying the competition binding assay (Carthew et al., *Cell* (1985), 43: 439-448). Unlabeled DNA probes for the competition assay were pre-incubated with nuclear extract in a binding buffer before the adding of the $^{32}$P end-labeled DNA probe. In this study, an additional mutant DNA probe was also used for the competition assay to confirm the specificity of DNA-protein complex, except for the three DNA probes (i.e., DNA probes A, B, and C) used in the standard binding reaction. The sequence of the mutant DNA probe was 5'-AAAGGGGACT ACAAAGGGGACTAC-3' (SEQ ID NO:15), which contained several nucleotide substitutions of the DNA probe A.

Antibody Supershift Assay.

A variation of the mobility shift DNA-binding assay was applied which used antibodies to identify proteins present in the protein-DNA complex (Kristie et al., *Proc. Natl. Acad. Sci. USA*. (1986), 83:3218-3222). A specific antibody was added to a binding reaction, in order to decide, whether a suspected protein, e.g., a transcription factor, involved in the formation of the DNA-protein complex in gel shift study. No effect should be observed when the protein recognized by the antibody was not involved in the complex formation. Two different expectations would be seen, i.e., either the complex formation was inhibited, or an antibody-protein-DNA ternary complex was formed. The latter could result in a further reduction in the mobility of the protein-DNA complex (i.e., supershift).

Purified recombinant Sp1 protein was purchased from Promega (USA). The Sp1 antibody (Santa Cruz Biotechnology) was incubated with nuclear extracts and DNA probes for 30 min.

Results

Motility Shift Assay with the DNA Probe A.

Figure 3A:
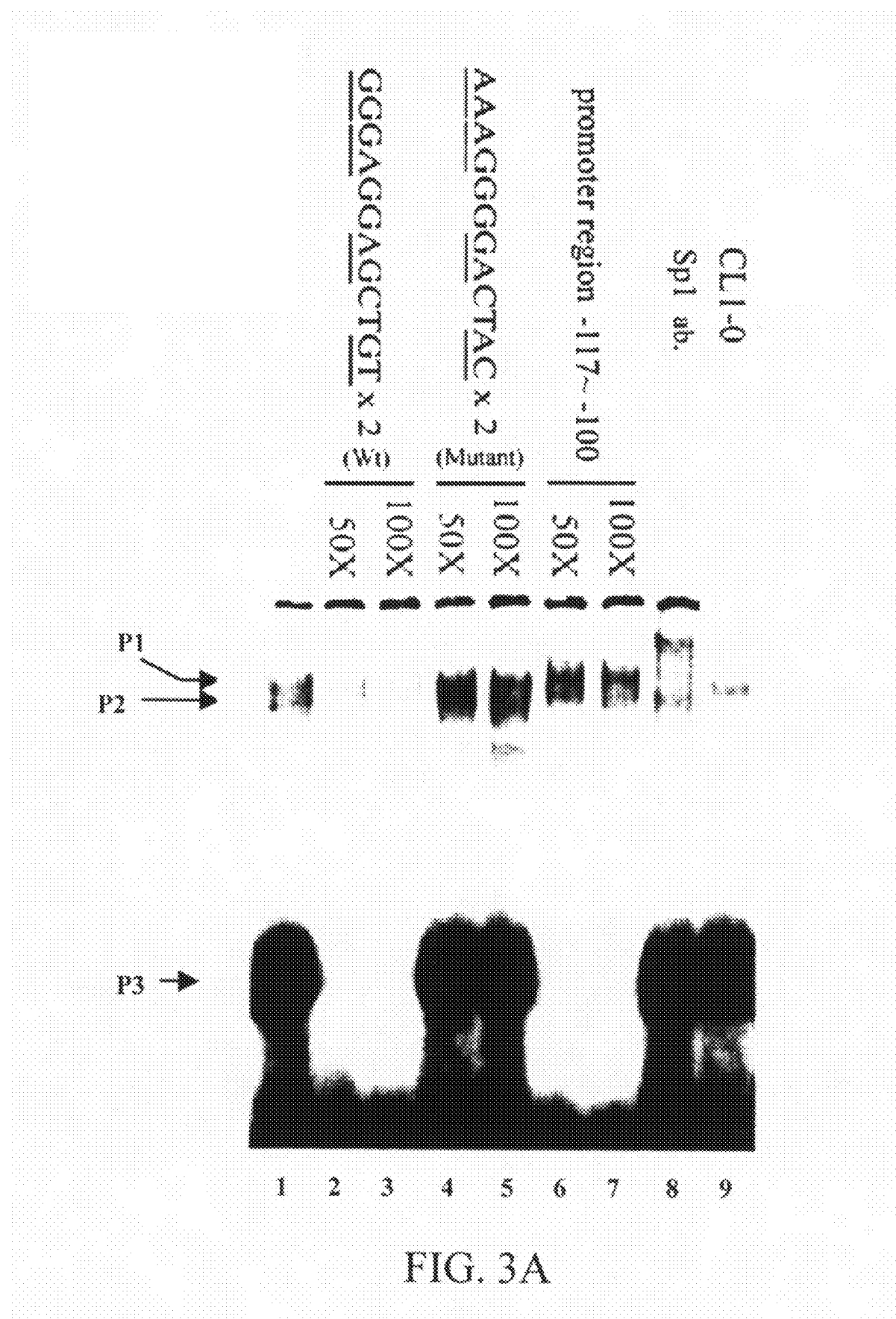
FIG. 3A: Lane 1, standard binding assay using HeLa nuclear extract and $^{32}P$ end labeled DNA probe A; Lane 2 and Lane 3: competition assay by adding 50 fold and 100 fold of the cold DNA probe A, respectively; prior to the addition of $^{32}P$ end-labelled DNA probe A; Lane 4 and Lane 5: competition binding assay by incubating 50 fold and 100 fold of the cold mutant probe (containing a repeat of AAAGGGGACTAC, SEQ ID NO:23), respectively, prior to the addition of $^{32}P$ end-labelled DNA probe A; Lane 6 and Lane 7: competition binding assay by incubating 50 fold and 100 fold of the cold DNA probe B, respectively, prior to the addition of $^{32}P$ end-labelled DNA probe A; Lane 8: antibody super shift assay with 0.8 μg Sp1 antibody; Lane 9: standard binding assay using $CL_{1-0}$ nuclear extract. Sequences labeled Wt and Mutant are disclosed as SEQ ID NOS 5 and 23, respectively.

Three specific DNA-protein complexes (P1, P2, and P3) were identified in the HeLa nuclear extracts using the DNA probe A containing the tandem repeat of the first regulatory factor binding site (FIG. 3A, lane 1). However, these DNA-protein complexes could be eliminated when an excess of 50-fold and 100-fold of the cold and unlabeled DNA probe A were competing in the competition mobility shift assay (FIG. 3A, lane 2 and lane 3). The DNA-protein complex P3 could also be inhibited by the unlabeled DNA probe B (FIG. 3A, lane 6 and lane 7), which contains a GGGAGGAG-inverted element. As expected, none was competed out by the unlabeled mutant DNA probe (FIG. 3A, lane 4 and lane 5). The results of this assay indicated that protein(s) formed in the complex P3 might be specific to the GGGAGGAG-element, since DNA probe A and DNA probe B contain the same element.

Two specific DNA-protein complexes were found in the $CL_{1-0}$ nuclear extracts. They appeared to be equivalent to the DNA-protein complex P1 and P3 (FIG. 3A, lane 9) observed as well as in the binding reaction using HeLa nuclear extracts, because of their similar motility on the PAGE gel.

Motility Shift Assay with the DNA Probe B.

Figure 3B:
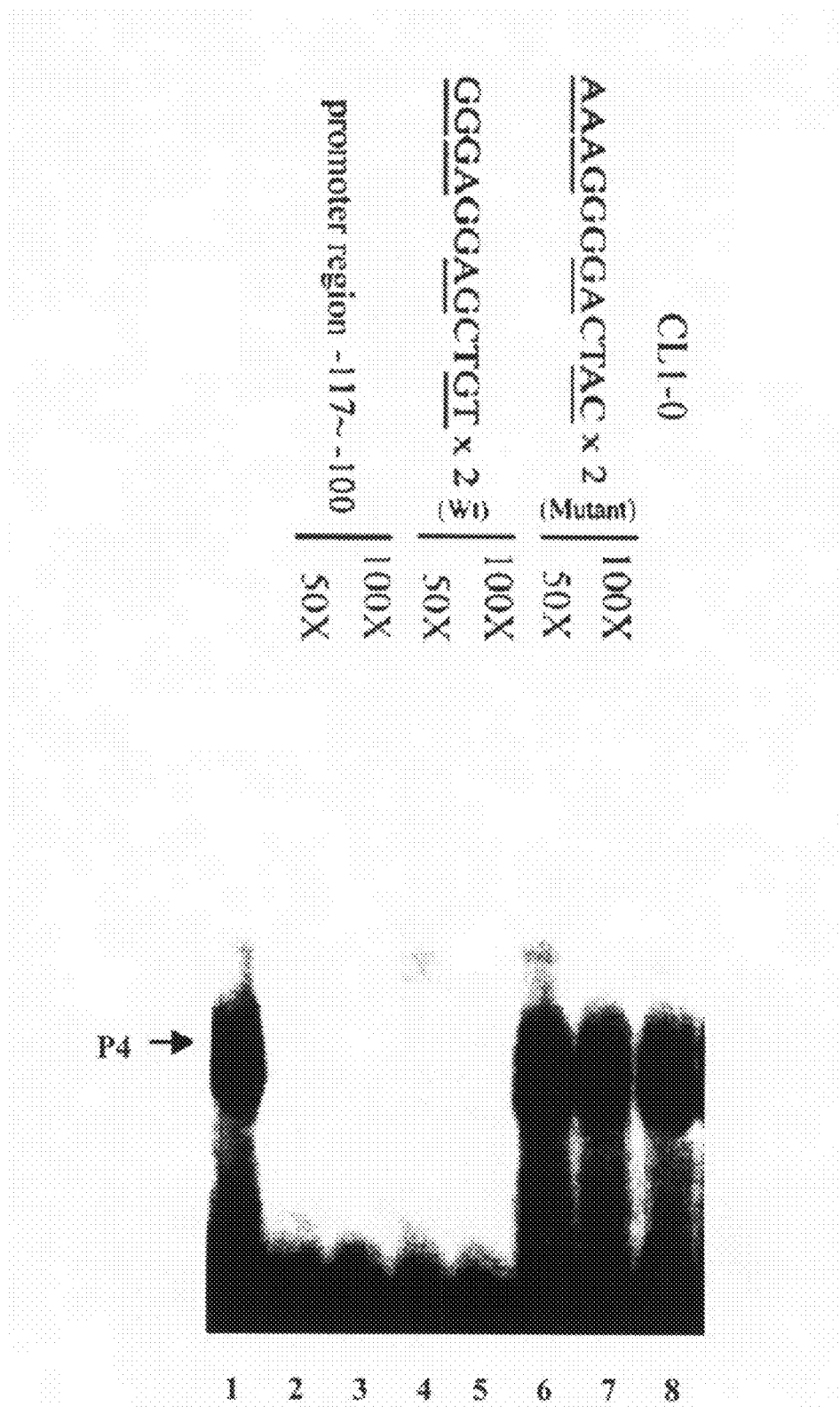
FIG. 3B: Lane 1: standard binding assay using HeLa nuclear extract and DNA probe B; Lane 2 and Lane 3: competition binfinh assay by incubating HeLa nuclear extract with 50 fold and 100 fold of the cold DNA probe B, respectively, prior to the addition of $^{32}P$ end-labelled DNA probe B; Lane 4 and Lane 5: competition binding assay by incubating HeLa nuclear extract with 50 fold and 100 fold of the cold DNA probe A, respectively, prior to the addition of $^{32}P$ end-labelled DNA probe B; Lane 6 and Lane 7: competition binding assay by incubating HeLa nuclear extract with 50 fold and 100 fold of the cold mutant probe (containing a repeat of AAAGGGGACTAC, SEQ ID NO:23), respectively, prior to the addition of $^{32}P$ end-labelled DNA probe B; Lane 8, standard binding assay using $CL_{1-0}$ nuclear extract. Sequences labeled Wt and Mutant are disclosed as SEQ ID NOS 5 and 23, respectively.

One major DNA-protein complex P4 could be detected both in the HeLa nuclear extracts and in the $CL_{1-0}$ nuclear extracts using the $^{32}P$ end-labelled DNA probe B (FIG. 3B, lane 1 and lane 8, respectively). The gel shift analysis shows the specificity of DNA-protein complex after the competition assay using the same unlabeled DNA fragment at the amount of an excess of 50-fold and 100-fold, respectively (FIG. 3B, lane 2 and lane 3). This DNA-protein complex disappeared when an excess of 50-fold and 100-fold unlabeled DNA probe A was added respectively (FIG. 3B, lane 4 and lane 5). The binding reaction with an excess of mutant DNA probe, as a negative control, was not able to compete with the specific DNA binding protein (FIG. 3B, lane 6 and lane 7). This gel shift study further confirmed that DNA probe A and DNA probe B possessed the same competition ability, since both contain the same sequence element (GGGAGGAG). Specifically, complex P3 and P4 might consist of the same components.

Motility Shift Assay with the DNA Probe C.

Figure 3C:
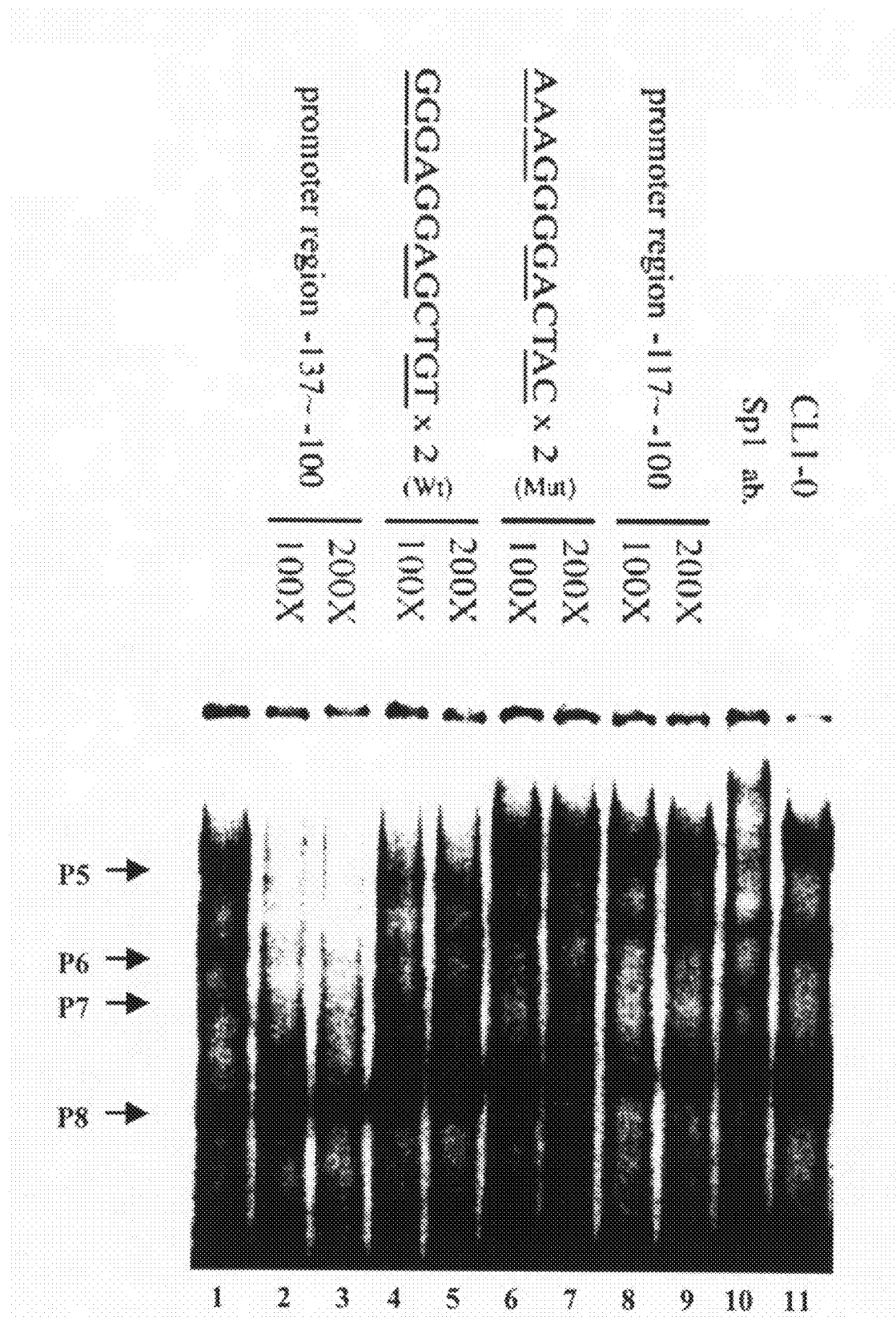
FIG. 3C: Lane 1: standard binding assay using HeLa nuclear extract; Lane 2 and Lane 3: competition binding assay by incubating HeLa nuclear extract with 100 fold and 200 fold of the cold DNA probe C, respectively, prior to the addition of $^{32}P$ end-labelled DNA probe C; Lane 4 and Lane 5: competition binding assay by incubating HeLa nuclear extract with 100 fold and 200 fold of the cold DNA probe A, respectively, prior to the addition of $^{32}P$ end-labelled DNA probe C; Lane 6 and Lane 7: competition binding assay by incubating HeLa nuclear extract with 100 fold and 200 fold of the cold mutant probe, respectively, prior to the addition of $^{32}$P end-labelled DNA probe C; Lane 8 and Lane 9: competition binding assay by incubating HeLa nuclear extract with 100 fold and 200 fold of the cold DNA probe B; Lane 10: super shift assay using 0.8 µg Sp1 antibody; Lane 11: standard binding assay using $CL_{1-0}$ nuclear extract. Sequences labeled Wt and Mutant are disclosed as SEQ ID NOS 5 and 23, respectively.

Four DNA-protein complexes P5, P6, P7, and P8 with decreasing molecular size in the HeLa nuclear extracts interacted with $^{32}P$ end-labelled DNA probe C were observed (FIG. 3C, lane 1). Three (P5, P6, and P7) of them appeared to be specific, since they were not detectable with an excess of 100-fold and 200-fold same unlabeled DNA probe C (FIG. 3C, lane 2 and lane 3). Competition assay with an excess of the mutant DNA probe shared the same pattern of the DNA-protein complexes as the standard binding assay (FIG. 3C, lane 6 and lane 7). The DNA-protein complex P5 and P6 were specifically competed by an excess of 100-fold and 200-fold of DNA probe A containing tandem repeat of the first regulatory factor element (FIG. 3C, lane 4 and lane 5), but not by the DNA probe B (FIG. 3C, lane 8 and lane 9). The DNA-protein complex P7 was assumed to be specific to the DNA probe B because it disappeared in the competition assay (FIG. 3C, lane 8 and lane 9). There could be additional protein(s), or transcription factor(s), specifically responsible for binding to the first regulatory factor binding site.

Three DNA-protein complexes were observed binding to DNA probe C using $CL_{1-0}$ nuclear extracts. They showed very similar motilities to those of the complex P5, P6, and P8 in the HeLa nuclear extracts (FIG. 3C, lane 11).

Antibody Supershift Assay of DNA-protein Complex.

The DNA-protein complex P1 with the slowest motility was supershifted by the addition of an anti-Sp1 antibody in the binding reaction (FIG. 3A, lane 8). The same effect could be seen for DNA Probe C-containing binding reaction (FIG. 3C, lane 10). A supershift effect of the DNA-protein complex with the slowest motility was confirmed by incubating $CL_{1-0}$ nuclear extract with DNA probe A and with DNA probe C (data not shown).

Motility Shift Assay with Additional Sp1 Protein.

Figure 3D:
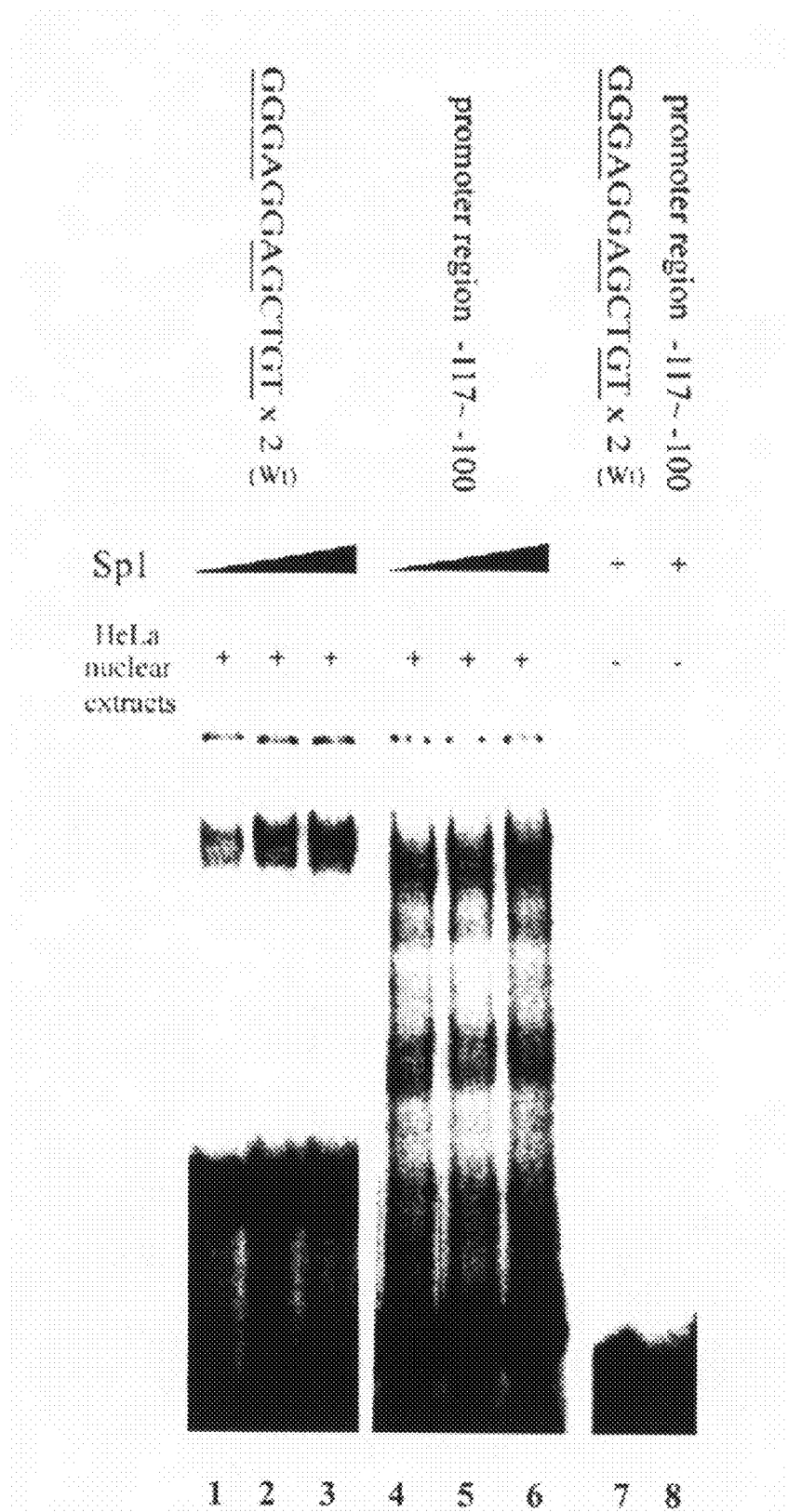
FIG. 3D: gel shift assay using various doses of recombinant Sp1 protein. Each binding reaction mixture contained $^{32}$P-labeled DNA probe (as indicated below) in HeLa nuclear extract and extra recombinant Sp1 protein. Lane 1 to Lane 3: $^{32}$P-end labeled DNA probe A was mixed with 0, 5 ng, 50 ng of recombinant Sp1 protein, respectively; Lane 4 to Lane 6: $^{32}$P-end labeled DNA probe C was mixed with 0, 5 ng, and 50 ng of recombinant Sp1 protein, respectively; Lane 7 and Lane 8: binding reaction mixture did not contain HeLa nuclear extract. Sequences labeled Wt are disclosed as SEQ ID NO: 5.

A further study to confirm the presence of Sp1 protein-forming complex was performed using the motility shift assay with additional Sp1 protein. We added extra 5 ng or 50 ng recombinant Sp1 protein to the binding reaction which contained the HeLa nuclear extract and $^{32}P$-labeled DNA probe A or DNA probe C. Stronger intensity of the DNA-protein complex with the slowest motility on gel shift assay was clearly found for both DNA probe A and DNA probe C (FIG. 3D, lane 1-3 and lane 4-6, respectively). The binding of Sp1 protein on the regulatory factor binding sites might be indirectly through the association with the other elements, since no signal was detected without the presence of nuclear extract (FIG. 3D, lane 7 and lane 8).

Summary of Motility Gel Shift Study Combined with Antibody Supershift Assay

The results shown above demonstrated that at least one type of Sp1 protein might be specifically involved in the formation of the DNA-protein complex by the application of commercial available specific anti-Sp1 antibody. It could further conclude that there were at least two other specific DNA-protein complexes required in the regulation of the transcription activity of CRMP-1 promoter.

Example 7

Transcriptional Regulation of SP1 Binding Protein for CRMP-1 Gene Nucleic Acid Regulatory Sequences Material and Methods Transient Co-transfection of Reporter DNA Constructs and Sp1 Protein-expressing Constructs.

Two reporter DNA constructs, pCRMP-1(−180/+50) and pCRMP-1(−99/+50), were separately transient co-transfected into DNA construct pSG5-Sp1 for over-expression of Sp1 protein. DNA construct pSG5 was used as the control in the cell line $CL_{1-0}$. Both DNA constructs, pSG5-Sp1 and pSG5, were kindly provided from Dr. Robert Tjian.

Reverse transcription-polymerase chain reaction (RT-PCR).

$CL_{1-0}$ cells were harvested after 24 h cultivation for RNA isolation using RNA-Bee™ kit. One microgram of total RNA was applied for reverse transcription reaction and 1/25 volume of the reverse transcription reaction mixture was further used for polymerase chain reaction (PCR) (Invitrogen). Three pairs of specific primers were designed for hCRMP-1, Sp-1, and Gp like gene expression study, as follows:

```
Primer pair for hCRMP-1:
sense primer
                                                   (SEQ ID NO: 16)
5'-ATGCCCTGAGCAGACCTGAAGAGC-3'
and antisense primer
                                                   (SEQ ID NO: 17)
5'-AGTAATGGGTGCCATCGGTCCCCAG-3'.

Primer pair for Sp-1:
sense primer
                                                   (SEQ ID NO: 18)
5'-GAGAGTGGCTCACAGCCTGTC-3'
and antisense primer
                                                   (SEQ ID NO: 19)
5'-GTTCAGAGCATCAGACCCCTG-3'.

Primer pair for G_β like (Shan, et al., Mol. Cell.
Biol. (1992) 12, 5620-5631)
sense primer
                                                   (SEQ ID NO: 20)
5'-GTAGGAACCTGGCTAACTG-3'
and antisense primer
                                                   (SEQ ID NO: 21)
5'-TACTGATAACTTCTTGCTTC-3'.
```

The expression of $G_\beta$ like was served as an internal control for RNA quantity. All results were visualized using ethidium bromide staining.

Results

The negative role of Sp1 in the crmp-1 promoter. The relative luciferase was used as indicator for the effect of over-expressed Sp I protein on regulatory activity. The over-expressed Sp1 protein in the cells co-transfected with the reporter construct pCRMP-1(−180/+50) resulted in the nearly 50% reduction of relative luciferase activity, in comparison with the cells without over-expression of Sp1 protein. As expected, no particular effect on the cells transfected with pCRMP-1(−99/+50) could be observed with or without over-expressed Sp1 protein, since the putative Sp1 binding sites are missing on this reporter DNA construct.

Figure 4:
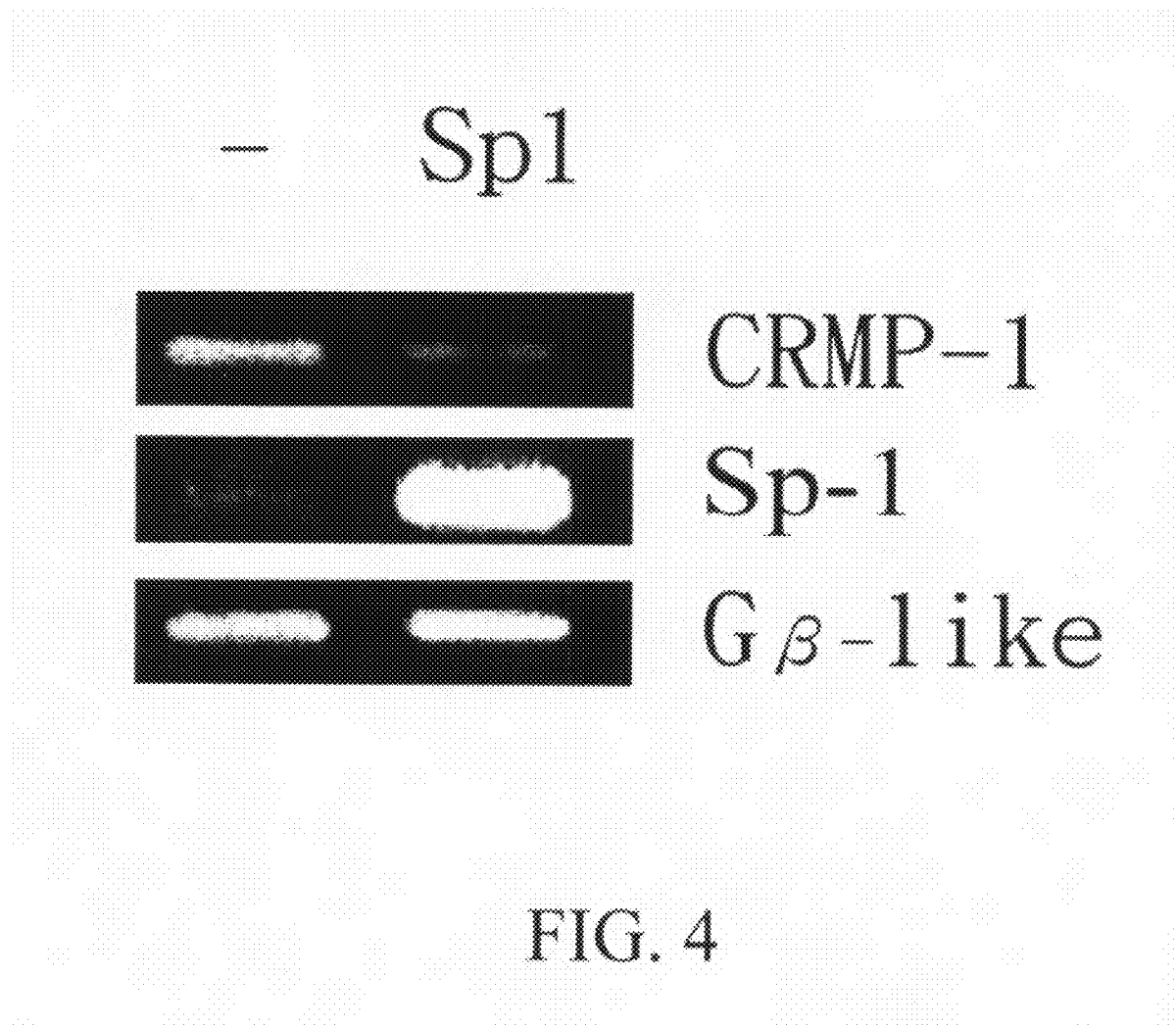
FIG. 4 shows the suppression effect of Sp1 on the transcription of the CRMP-1 gene in $CL_{1-0}$ cell line. Two DNA constructs, pSG5 (control) and pSG5-Sp1 (which could overexpress Sp1 protein) were separately co-transfected into $CL_{1-0}$ cells containing DNA construct pCRMP-1 (which contained the reporter luciferase gene and the CRMP-1 regulatory sequence at positions −180/+50). Left column: agarose gel electrophoresis indirectly demonstrating the levels of DNA corresponding to CRMP-1, Sp1, and Gβ-like protein in $CL_{1-0}$ cells co-transfected with pSG5 and pCRMP-1. A semi-quantitative assay was carried out by the reverse transcription (RT) using 1 microgram of total RNA at the first step and followed with a PCR using 1/25 volume of the first reaction product. Right column: levels of mRNA corresponding to CRMP-1, Sp1, and Gβ-like protein in $CL_{1-0}$ cells co-transfected with pSG5-Sp1 and pCRMP-1. All results were visualized using ethidium bromide staining.

Reverse transcription-polymerase chain reaction (RT-PCR) was used to evaluate the RNA level for CRMP-1 gene, Sp1 gene and $G_\beta$ like gene. The presence of the CRMP-1 RNA level was significantly decreased, as Sp1 protein was over-expressed in cells (FIG. 4). The RNA level of the $G_\beta$ like gene (a house keeping gene used as the experimental control) showed similar RNA level (FIG. 4). As expected, the RNA level of Sp1 was noticeably higher in cells transfected with Sp1 over-expressed DNA construct. These results confirmed that the Sp1 protein might possibly act as a negative regulator for CRMP-1 expression.

While the invention has been described by way of examples and in term of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. An isolated transcription unit consisting of the nucleic acid of SEQ ID NO:3.

2. The isolated transcription unit according to claim 1, wherein said nucleic acid sequence is a nucleic acid regulatory sequence of a gene encoding a collapsing response mediator protein-1 (CRMP-1) in humans.

3. A polynucleic acid construct comprising:
   a) an isolated transcription unit comprising the nucleic acid of SEQ ID NO: 3; and
   b) a reporter gene operatively linked to said transcription unit.

4. The polynucleic acid construct according to claim 3, wherein said reporter gene encodes a firefly luciferase.

5. A DNA construct comprising an isolated transcription unit comprising the nucleic acid of SEQ ID NO: 3 and a vector, wherein said vector is a pGL3-basic vector.

6. An isolated transfected cell comprising a DNA construct comprising:
   a) an isolated transcription unit comprising the nucleic acid of SEQ ID NO: 3; and
   b) a reporter gene operatively linked to the transcription unit,
   wherein said transfected cell is a human cell.

7. The transfected cell according to claim 6, wherein said human cell is a human cancer cell.

8. The transfected cell according to claim 7, wherein said human cancer cell is a human lung adenocarcinoma cell or a human colon cancer cell.

9. A method for assaying the transcriptional activity of a reporter gene in a host cell in vitro, comprising the steps of:
   a) transfecting a host cell with a DNA construct comprising:
      (i) an isolated transcription unit comprising the nucleic acid of SEQ ID NO: 3; and
      (ii) a reporter gene operatively linked to the transcriptional unit; and
   b) measuring the activity of the reporter gene and thereby assaying the transcriptional activity of the reporter gene.

10. The method according to claim 9, wherein said host cell is a human cell.

* * * * *

SEQUENCE LISTING

```
<160> NUMBER OF SEQ ID NOS: 24

<210> SEQ ID NO 1
<211> LENGTH: 2109
<212> TYPE: DNA
<213> ORGANISM: Homo sapiens

<400> SEQUENCE: 1
gctttgtacc ggcgaaatct gcttgggagc agcgatctgt ttggccagtg gcaggcggat      60
gctcctcccc ctgatacgca cgtggtcttg tcccttgctg tagggctttt ctgctcagat     120
ctccagactg acccagggaa acgccctggt acggggaacc taggacttaa caactccaag     180
gaagggagtg taggagttgg ggagggacag tgtccccatc tgcaatttcc ggtcattgac     240
agggatttta ggccccgctg agagccaggg atgcatgaat gcgtggaggg aaatgagttg     300
taaacagagt gtaggggaac ctggcatctc catgctgctt tgctgcagct aatatgtttt     360
gcacccgggg tacatcattt tacctctgta agcctcaatt tcctgtctgt aaaatgggaa     420
aattatgcct agtgttcctg ggatactgag ctggcttctc tgtgaagcta aaacctcacc     480
tctattttaa ggcccaggtg tctctggcct cctgccctgg attagggggac tggcccctgg     540 ggtggtgaag gtcagggccc cagcccccaa ccacagtgct gggggagctg taccaagcct     600
aggccaccct cgctctggat ggcaacttga aagcagaaaa gatgagtagt ttcataggac     660
ctgtggggtt ggatttcgca tgcagaaaat gaacaacgaa gtggtggaca aggttggtgt     720
tttattctgc ctgggaactt ggggcacctg tccagtgagg ttggggcttg ctggggctcc     780
```

```
cccttttcct ccatcttctt tcatcttttc ccctctgctg ttacggacct tgtcaagctg      840
tgacctggct tcctgcccac ctccctctgg agcaacatct ggatcatgga ctccggggct      900
ggtgtccaca gtgctgggag gcaggagcac cctagtcctc ctcctgaccc ccagcttgtc      960
cccagggctg tggagacctt ggtgccagtg cccagcccct ccaaacacct gctgtcttgg     1020
aggcaattct gtggggtgac ctggtggccc cagtgtcagg ctgctgtgtg atgagggagc     1080
tgctgttgga gtagaacagg tcagcattaa ttaaggccgt accttctgt ccctgctgtt      1140 ccctctgcca gttaggggc tccaccttag aggcccccag ggagggctgg ttcaatgcta      1200
ggatggagag ggtggcaggg agaggcttcg tggtggggaa ggcattggag atgggtctag     1260
gggagtggac aggctttgt ctggggtaga ctattcaggg agagggtaca gcgtgaataa      1320
aggcttgggt tccgagatgg aaaaagtgct tggtgcattc agggagaggc actcgggaag     1380
gataaacgga ggctatggaa ggagaggcaa gaggggagcg gtccttgggc gcgatcctgg     1440
agggacaaga acgttcccag cagcttgggc cgatccttgg cccccgtccc acactccctc     1500
cccccacacc cccgcagatg ttccggggag gcctccagac gcgcggccac acacctgtgg     1560
cgccgcccgc gggccctgac cgcgccgtct ttttcttta aaggagccct gaaaaccata      1620
ctctctggat cgcgagagcg aggccagggc ccgccaaggg cgtgtgcgca gggcggggt      1680 cggcggggct gggcggtgg ggggcggggg cggggtggg agatcggaag ggaagcgctt       1740
cctggttcga gccgagaggg gcgaatccgg cttcgctccg cgccgccggg aggagctgtc     1800
tgcagccccc tcctcccgcc ctcgcctctc cctcctcctt ctcccgccct cctcgccgat     1860
ccgggcggtg ctggcagccg gagcggcggc gggcgggccg agcagccggg gcagccgcgc     1920
gtgggcatcc acgggcgccg agcctccgtc cgtgtctcta tccctcccgg gcctttgtca     1980
gcgcgcccgc tgggagcggg gccgagagcg ccggttccag tcagacagcc ccgcaggtca     2040
gcggccgggc cgagggcgcc agaggggggcc atgtcgtacc agggcaagaa gagcatcccg     2100
cacatcacg                                                             2109
```

<210> SEQ ID NO 2
<211> LENGTH: 1970
<212> TYPE: DNA
<213> ORGANISM: Homo sapiens

<400> SEQUENCE: 2

```
gctttgtacc ggcgaaatct gcttgggagc agcgatctgt ttggccagtg gcaggcggat       60
gctcctcccc ctgatacgca cgtggtcttg tcccttgctg taggggcttt ctgctcagat      120
ctccagactg acccagggaa acgccctggt acggggaacc taggacttaa caactccaag      180
gaagggagtg taggagttgg ggaggacag tgtccccatc tgcaatttcc ggtcattgac       240
agggatttta ggccccgctg agagccaggg atgcatgaat gcgtggaggg aaatgagttg      300
taaacagagt gtaggggaac ctggcatctc catgctgctt tgctgcagct aatatgtttt      360
gcacccgggg tacatcattt tacctctgta agcctcaatt tcctgtctgt aaaatgggaa      420
aattatgcct agtgttcctg ggatactgag ctggcttctc tgtgaagcta aaacctcacc      480 tctatttaa ggcccaggtg tctctggcct cctgccctgg attaggggac tggcccctgg      540
ggtggtgaag gtcagggccc cagccccaa ccacagtgct gggggagctg taccaagcct       600
aggccaccct cgctctggat ggcaacttga aagcagaaaa gatgagtagt ttcataggac      660
ctgtggggtt ggatttcgca tgcagaaaat gaacaacgaa gtggtggaca aggttggtgt      720
tttattctgc ctgggaactt ggggcacctg tccagtgagg ttggggcttg ctggggctcc     780
```

```
cccttttcct ccatcttctt tcatctttttc ccctctgctg ttacggacct tgtcaagctg       840
tgacctggct tcctgcccac ctccctctgg agcaacatct ggatcatgga ctccggggct       900
ggtgtccaca gtgctgggag gcaggagcac cctagtcctc ctcctgaccc ccagcttgtc       960
cccagggctg tggagacctt ggtgccagtg gcccagccct ccaaacacct gctgtcttgg      1020
aggcaattct gtggggtgac ctggtggccc cagtgtcagg ctgctgtgtg atgagggagc      1080
tgctgttgga gtagaacagg tcagcattaa ttaaggccgt acccttctgt ccctgctgtt      1140
ccctctgcca gttaggggc tccaccttag aggcccccag ggagggctgg ttcaatgcta      1200
ggatggagag ggtggcaggg agaggcttcg tggtggggaa ggcattggag atgggtctag      1260
gggagtggac aggctttgt ctggggtaga ctattcaggg agagggtaca gcgtgaataa      1320
aggcttgggg tccgagatgg aaaaagtgct tggtgcattc agggagaggc actcgggaag      1380
gataaacgga ggctatggaa ggagaggcaa gaggggagcg gtccttgggc gcgatcctgg      1440
agggacaaga acgttcccag cagcttgggc cgatccttgg cccccgtccc acactccctc      1500
cccccacacc cccgcagatg ttccggggag gcctccagac gcgcggccac acacctgtgg      1560
cgccgcccgc gggccctgac cgcgccgtct ttttctttta aaggagccct gaaaaccata      1620
ctctctggat cgcgagagcg aggccagggc ccgccaaggg cgtgtgcgca gggcgggggt      1680
cggcggggct gggcgggtgg ggggcggggg cggggtgggg agatcggaag ggaagcgctt      1740
cctggttcga gccgagaggg gcgaatccgg cttcgctccg cgccgccggg aggagctgtc      1800
tgcagccccc tcctcccgcc ctcgcctctc cctcctcctt ctcccgccct cctcgccgat      1860
ccgggcggtg ctggcagccg gagcggcggc gggcgggccg agcagccggg gcagccgcgc      1920
gtgggcatcc acgggcgccg agcctccgtc cgtgtctcta tccctcccgg                  1970

<210> SEQ ID NO 3
<211> LENGTH: 230
<212> TYPE: DNA
<213> ORGANISM: Homo sapiens

<400> SEQUENCE: 3
cctggttcga gccgagaggg gcgaatccgg cttcgctccg cgccgccggg aggagctgtc        60
tgcagccccc tcctcccgcc ctcgcctctc cctcctcctt ctcccgccct cctcgccgat       120
ccgggcggtg ctggcagccg gagcggcggc gggcgggccg agcagccggg gcagccgcgc       180
gtgggcatcc acgggcgccg agcctccgtc cgtgtctcta tccctcccgg                  230

<210> SEQ ID NO 4
<211> LENGTH: 81
<212> TYPE: DNA
<213> ORGANISM: Homo sapiens

<400> SEQUENCE: 4
cctggttcga gccgagaggg gcgaatccgg cttcgctccg cgccgccggg aggagctgtc        60
tgcagccccc tcctcccgcc c                                                  81

<210> SEQ ID NO 5
<211> LENGTH: 12
<212> TYPE: DNA
<213> ORGANISM: Homo sapiens

<400> SEQUENCE: 5
gggaggagct gt                                                            12
```

<210> SEQ ID NO 6
<211> LENGTH: 16
<212> TYPE: DNA
<213> ORGANISM: Homo sapiens

<400> SEQUENCE: 6 cccctcctc ccgccc                                                        16

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccgctcgagg ctttgtaccg gcgaaatct                                         29

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cccaagcttc gtgattgtgc gggatgctct                                        30

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgctaattac gccagcccaa g                                                 21

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cccaagcttc cgggagggat agagacac                                          28

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ccgctcgagg ggaggagctg tgggaggagc tgtctcgagc gg                          42

<210> SEQ ID NO 12
<211> LENGTH: 24
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 12
gggaggagct gtgggaggag ctgt                                              24

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13 agcccctcc tcccgccc                                                      18

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
cgccgggagg agctgtctgc agcccctcc tcccgccc                                38

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15 aaagggact acaaagggga ctac                                               24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atgccctgag cagacctgaa gagc                                              24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agtaatgggt gccatcggtc cccag                                             25

<210> SEQ ID NO 18
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 18
gagagtggct cacagcctgt c                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gttcagagca tcagacccct g                                              21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtatggaacc tggctaactg                                                20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tactgataac ttcttgcttc                                                20

<210> SEQ ID NO 22
<211> LENGTH: 240
<212> TYPE: DNA
<213> ORGANISM: Homo sapiens

<400> SEQUENCE: 22
ggaagcgctt cctggttcga gccgagaggg gcgaatccgg cttcgctccg cgccgccggg    60
aggagctgtc tgcagccccc tcctcccgcc ctcgcctctc cctcctcctt ctcccgccct   120
cctcgccgat ccgggcggtg ctggcagccg gagcggcggc gggcgggccg agcagccggg   180
gcagccgcgc gtgggcatcc acgggcgccg agcctccgtc cgtgtctcta tccctcccgg   240

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 aaagggact ac                                                         12

<210> SEQ ID NO 24
<211> LENGTH: 1719
```

<212> TYPE: DNA
<213> ORGANISM: Homo sapiens
<220> FEATURE:
<223> OTHER INFORMATION: nucletoide seqeunce encoding CRMP-1 protein
<308> DATABASE ACCESSION NUMBER: GenBank/D78012 and GenBank/BAA11190

<400> SEQUENCE: 24

```
atgtcgtacc agggcaagaa gagcatcccg cacatcacga gtgaccgact cctcatcaaa      60
ggtggacgga tcatcaacga tgaccaatcc ctttatgctg acgtctacct ggaggatgga     120
cttatcaaac aaataggaga gaacttaatc gttcctggtg gagtgaagac cattgaagcc     180
aacgggcgga tggttattcc cggaggtatt gatgtcaaca cgtacctgca gaagccctcc     240
caggggatga ctgcggctga tgacttcttc aagggacca gggcggcact ggtgggcggg      300
accacgatga tcattgacca tgttgttcct gaacctgggt ccagcctact gacctctttc     360
gagaagtggc acgaagcagc tgacaccaaa tcctgctgtg attactccct ccacgtggac     420
atcacaagct ggtacgatgg cgttcgggag gagctggagg tgctggtgca ggacaaaggc     480
gtcaattcct ccaagtcta catggcctat aaggatgtct accaaatgtc cgacagccag     540
ctctatgaag ccttttacctt ccttaagggc ctgggagctg tgatcttggt ccatgcagaa     600
aatggagatt tgatagctca ggaacaaaag cggatcctgg agatgggcat cacgggtccc     660
gagggccatg ccctgagcag acctgaagag ctggaggccg aggcggtgtt ccgggccatc     720
accattgcgg gccggatcaa ctgccctgtg tacatcacca aggtcatgag caagagtgca     780
gccgacatca tcgctctggc caggaagaaa gggcccctag ttttttggaga gcccattgcc     840 gccagcctgg ggaccgatgg cacccattac tggagcaaga actgggccaa ggctgcggcg     900
ttcgtgactt ccctctccct gagcccggac cctaccacgc ccgactactt gacctcccta     960
ctggcctgtg gggacttgca ggtcacaggc agcggccact gtccctacag cactgcccag    1020
aaggcggtgg gcaaggacaa ctttaccctg atccccgagg gtgtcaacgg gatagaggag    1080
cggatgaccg tcgtctggga caaggcggtg gctactggca aaatggatga gaaccagttt    1140
gtcgctgtca ccagcaccaa tgcagccaag atctttaacc tgtacccaag gaaagggcgg    1200
attgccgtgg gctcggatgc cgacgtggtc atctgggacc ccgacaagtt gaagaccata    1260
acagccaaaa gtcacaagtc ggcggtggag tacaacatct tcgagggtat ggagtgccac    1320
ggctccccac tagtggtcat cagccagggc aagatcgtct ttgaagacgg aaacatcaac    1380
gtcaacaagg gcatgggccg cttcattccg cggaaggcgt tcccggagca cctgtaccag    1440
cgcgtcaaaa tcaggaataa ggttttttgga ttgcaagggg tttccagggg catgtatgac    1500
ggtcctgtgt acgaggtacc agctacaccc aaatatgcaa ctcccgctcc ttcagccaaa    1560
tcttcgcctt ctaaacacca gccccaccc atcagaaacc tccaccagtc aacttcagc     1620 ttatcaggtg cccagataga tgacaacaat cccaggcgca ccggccaccg catcgtggcg    1680 cccctggtg gccgctccaa catcaccagc ctcggttga                            1719
```